United States Patent

Bagge

(10) Patent No.: US 9,386,964 B2
(45) Date of Patent: Jul. 12, 2016

(54) 3D VIEW OF 2D ULTRASOUND IMAGES

(75) Inventor: Jan Peter Bagge, Stenloese (DK)

(73) Assignee: B-K Medical Aps, Herlev (DK)

( * ) Notice: Subject to any disclaimer, the term of this patent is extended or adjusted under 35 U.S.C. 154(b) by 220 days.

(21) Appl. No.: 13/818,999

(22) PCT Filed: Aug. 31, 2010

(86) PCT No.: PCT/IB2010/002146
§ 371 (c)(1),
(2), (4) Date: Feb. 26, 2013

(87) PCT Pub. No.: WO2012/028896
PCT Pub. Date: Mar. 8, 2012

(65) Prior Publication Data
US 2013/0158405 A1    Jun. 20, 2013

(51) Int. Cl.
*A61B 8/08* (2006.01)
*G01S 7/52* (2006.01)
(Continued)

(52) U.S. Cl.
CPC .................. *A61B 8/5253* (2013.01); *A61B 8/08* (2013.01); *A61B 8/145* (2013.01); *A61B 8/4438* (2013.01); *A61B 8/4488* (2013.01); *A61B 8/466* (2013.01); *A61B 8/467* (2013.01); *A61B 8/481* (2013.01); *A61B 8/485* (2013.01); *A61B 8/488* (2013.01); *G01S 7/52068* (2013.01); *G01S 7/52074* (2013.01); *G01S 15/8993* (2013.01); *A61B 8/461* (2013.01); *A61B 8/483* (2013.01)

(58) Field of Classification Search
CPC ........ A61B 8/08; A61B 8/145; A61B 8/4438; A61B 8/4488; A61B 8/466

USPC ................................... 600/437, 443, 447, 449
See application file for complete search history.

(56) References Cited

U.S. PATENT DOCUMENTS 4,694,434 A    9/1987    von Ramm et al.
5,546,807 A    8/1996    Oxaal et al.
(Continued)

FOREIGN PATENT DOCUMENTS

| JP | H04-314435 | 5/1992 |
| JP | H05-317309 | 3/1993 |
| JP | H09-192131 | 7/1997 |

OTHER PUBLICATIONS

International search report for PCT/IB2010/002146 published as WO 2012/028896 A1.
(Continued)

*Primary Examiner* — Baisakhi Roy
(74) *Attorney, Agent, or Firm* — Anthony M. Del Zoppo, III; Driggs, Hogg, Daugherty & Del Zoppo, Co., LPA

(57) ABSTRACT

A method includes generating a single three dimensional perspective or axonometric image based on at least two two-dimensional intersecting scanplanes. A rendering engine includes a view processor that generates a single three dimensional perspective image based on at least two two-dimensional intersecting scanplanes. An ultrasound imaging system includes a transducer array, including at least two one dimensional transducer arrays, each receiving echoes corresponding to different intersecting scanplanes, a scan converter that scan converts the echoes into a format for display on a monitor, and a view processor that combines the intersecting scanplanes to form a single three dimensional perspective image.

24 Claims, 4 Drawing Sheets

(51) Int. Cl.
*G01S 15/89* (2006.01)
*A61B 8/14* (2006.01)
*A61B 8/00* (2006.01)

(56) References Cited

U.S. PATENT DOCUMENTS

| | | | |
|---|---|---|---|
| 6,761,689 B2 | 7/2004 | Salgo et al. | |
| 2003/0013955 A1* | 1/2003 | Poland | 600/437 |
| 2003/0023166 A1* | 1/2003 | Frisa et al. | 600/443 |
| 2004/0168517 A1* | 9/2004 | Dufait | B06B 1/0622 73/626 |
| 2005/0085730 A1* | 4/2005 | Flesch et al. | 600/459 |
| 2005/0187474 A1 | 8/2005 | Kwon | |
| 2005/0228278 A1* | 10/2005 | Chalana et al. | 600/437 |
| 2008/0146932 A1* | 6/2008 | Chalana et al. | 600/447 |
| 2008/0319318 A1* | 12/2008 | Johnson et al. | 600/445 |
| 2009/0112089 A1* | 4/2009 | Barnard et al. | 600/443 |
| 2009/0156940 A1* | 6/2009 | Yen et al. | 600/459 |
| 2010/0036252 A1* | 2/2010 | Chalana et al. | 600/449 |
| 2010/0106023 A1* | 4/2010 | Ogawa | A61B 8/12 600/463 |

OTHER PUBLICATIONS

JP2013-526556; Japanese First Office Action, dated Feb. 25, 2014.

* cited by examiner

3D VIEW OF 2D ULTRASOUND IMAGES

RELATED APPLICATION

This application is a national filing of PCT application Serial No. PCT/IB2010/002146, filed Aug. 31, 2010, published as WO 2012/028896A1 on Mar. 8, 2012.

TECHNICAL FIELD

The following generally relates to ultrasound (US) imaging and more particularly to generating a three dimensional (3D) view such as a perspective, axonometric and/or other three dimensional view based on intersecting two dimensional (2D) US images.

BACKGROUND

Ultrasound imaging has provided useful information about the interior characteristics of an object or subject under examination. One US scanner has included a one dimensional transducer array with 64 to 192 transducer elements. Such a one dimensional transducer array has been used to acquire echoes corresponding to an axial plane (or two dimensional slice, which is transverse to a longitudinal axis) of an organ(s) and/or structure (e.g., a biopsy needle) in the body. In B-mode imaging, the echoes have been used to generate scanlines, and the scanlines have been used to generate a scanplane, or two dimensional image of the plane, which can be displayed via a monitor. With frame rates of 10 Hz or greater, the B-mode scanplanes can be combined with color flow, Doppler flow, elastography, contrast harmonic, and/or other information requiring higher frame rates.

In order to additionally view a plane in another orientation (e.g., sagittal, or along the longitudinal axis), the clinician has to rotate the transducer head to the other orientation. In response to rotating the transducer head, the displayed two dimensional axial image is replaced by an image from the other orientation. In order to utilize the images from both orientations, the clinician must make a mental image of (or memorize) the axial image and then mentally construct a three dimensional view based on the mental image of the axial image and the displayed image from the other orientation. Unfortunately, it may take years of experience before a clinician is able to mentally construct the three dimensional image, the mental image is susceptible to human error, and the two images used to construct the three dimensional image do not reflect the same point in time.

One technique for concurrently acquiring and displaying intersecting images of different planes is to use a biplane transducer, such as transducer Type 8814, a product of BK Medical, Herlev, DK. Generally, a biplane transducer includes two separate one dimensional transducer arrays arranged with respect to each other to concurrently acquire data corresponding to two different and intersecting planes (e.g., axial and sagittal planes). Using a biplane transducer mitigates having to rotate the transducer head from one orientation to another orientation to acquire intersecting images of multiple planes, and the images are acquired at the same time. However, the images have been presented side-by-side. As a consequence, the clinician still has to mentally combine the images to construct a three dimensional view.

A two dimensional transducer array allow for simultaneously acquiring a three dimensional volume of data. Ray casting or other techniques have been used to select data for one or more planes of interest, such as two intersecting planes, which can then be volume rendered in a three dimensional view. However, with two dimensional transducer arrays, relatively lower frame rates (e.g., on the order of 2-5 Hz) generally are utilized in order to simultaneously acquire the large volume of data (e.g., 16K, or 128×128). Unfortunately, such lower frame rates are not well-suited for applications including color flow, Doppler flow, elastography, contrast harmonic, etc., which require higher data rates. Furthermore, two dimensional transducer arrays generally include a lot more transducer elements than their one dimensional counterparts (e.g., 16K to 128 in the above examples), which tends to make two dimensional transducer arrays significantly more costly than one dimensional transducer arrays.

SUMMARY

Aspects of the application address the above matters, and others.

In one aspect, a method includes generating a single three dimensional perspective image based on at least two two-dimensional intersecting scanplanes.

In another aspect, a rendering engine includes a perspective or axonometric view processor that generates a single three dimensional perspective image based on at least two two-dimensional intersecting scanplanes.

In another aspect, an ultrasound imaging system includes a transducer, including at least two one dimensional transducer arrays, each receiving echoes corresponding to a different intersecting scanplanes, a scan converter that scan converts the echoes into a format for display on a monitor, and a view processor that combines the intersecting scanplanes to form a single three dimensional perspective image.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which.

DETAILED DESCRIPTION

Figure 1:
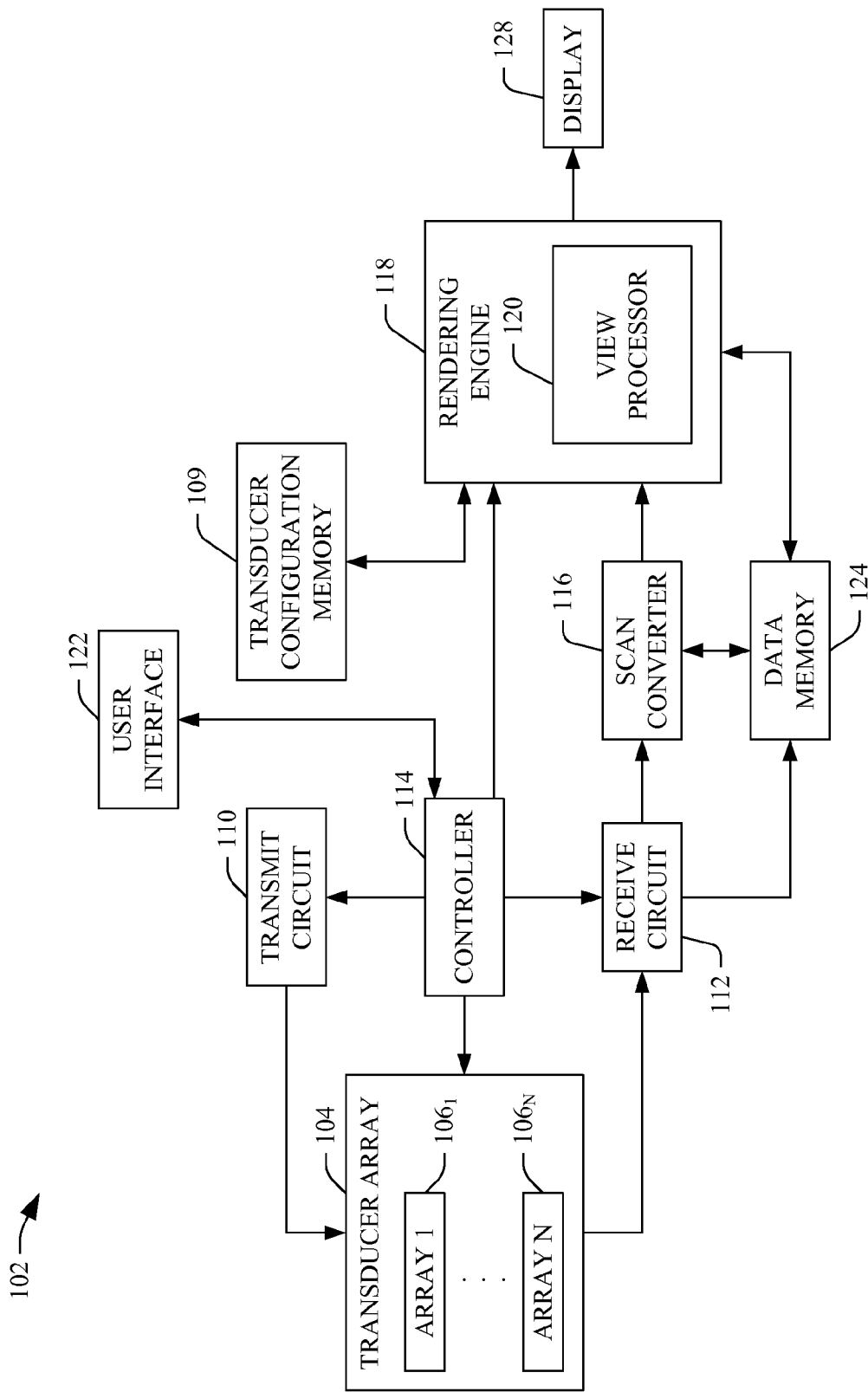
FIG. 1 illustrates an example imaging system.

FIG. 1 illustrates an imaging system 102 such as ultrasonic imaging system. The imaging system 102 includes a transducer 104 with N (where N is an integer equal to or greater than one) one-dimensional arrays $106_1, \ldots, 106_N$ (collectively referred to herein as arrays 106), each having one or more transducer elements (e.g., 16, 64, 128, 196, 256, etc. elements). Individual arrays 106 may include linear and/or curved shaped arrays, and the different arrays 106 can be employed individually, simultaneously or in an interleaved manner to acquire data with frame rates in a range of one (1) to two hundred (200) Hertz (Hz) for A-mode, B-mode, etc. acquisitions, individually and in combination with color flow, Doppler flow, elastography, contrast harmonic, and/or other information. In another embodiment, at least one of the arrays 106 is a two dimensional array.

With the illustrated embodiment, at least two of the arrays 106 are physically arranged with respect to each other in the transducer array 104 so as to facilitate imaging at least M (where M is an integer equal to or greater than one) difference scanplanes through an object of interest or subject, including intersecting and/or non-intersecting planes. In one instance, the at least two arrays 106 and 108 are physically arranged so that one of the arrays images a substantially axial plane, which is transverse to a longitudinal axis of the subject or object being scanned, concurrently while another of the arrays images a different plane such as a substantially sagittal plane, which is along the longitudinal axis, while the transducer array 104 remains at substantially a same position relative to the subject or object of interest. Such planes generally are ninety (90) degrees apart; however, other angles between zero (0) and one hundred eighty (180) are also contemplated herein. In another instance, the arrays 106 and 108 are serially or otherwise utilized.

In one embodiment, the transducer array 104 is part of a biplane transducer, having two one dimensional arrays of transducer elements. An example of such a transducer array is the Intraoperative Transducer Type 8814, a product of BK Medical, Herlev, DK, which is a V-shaped biplane transducer having two one dimensional arrays physically arranged for simultaneously scanning two intersecting planes by interleaving scanline acquisitions. Such a biplane transducer array is well-suited for capturing information for tracking a location of structure such as a biopsy needle or the like in the object of interest and/or moving through the object of interest. Other transducer arrays, for example, transducer arrays including a two dimensional array or a single one dimensional array, can additionally or alternatively be utilized with the system 102.

Transducer configuration memory 109 stores information about the transducer array 104. For example, where the transducer array 104 includes a biplane transducer array, the configuration memory 109 stores information such as the angle between the planes of the biplane transducer array, the intersection region of the planes, etc. Such information can be provided in electronic format or otherwise by the manufacturer of the transducer array 104. This information may be stored as a look up table or otherwise, and retrieved in response to the system 102 identifying the transducer array 104 installed therewith, automatically and/or manually, for example, via a handshake and/or input provided by a user.

A transmit circuit 110 controls the phasing and/or time of actuation of each of the elements of the transducer array 104, which allows for steering and/or focusing the transmitted beam from predetermined origins along the array and at predetermined angles. A receive circuit 112 receives the echoes received by the transducer array 104. For B-mode and other applications, the receive circuit 112 beamforms (e.g., delays and sums) the echoes from the transducer elements into a sequence of focused, coherent echo samples along focused scanlines of a scanplane. The receive circuit 112 may also be configured to variously process the scanlines, for example, to lower speckle and/or improve specular reflector delineation via spatial compounding and/or other processing such as FIR filtering, IIR filter, etc.

A controller 114 controls the transmit circuit 110 and/or the receive circuit 112. Such control may include, but is not limited to, controlling the frame rate, number of scanline groups, transmit angles, transmit energies, transmit frequencies, transmit and/or receive delays, etc. Higher frame rate (e.g., real-time or near real-time) applications may be acquired on the order of 10 or more Hz, such as 20-200 Hz, and lower frame rate applications may be acquired on the order of 10 or less Hz.

A scan converter 116 scan converts the frames of data to generate data for display, for example, by converting the data to the coordinate system of the display. This may include changing the vertical and/or horizontal scan frequency of signal based on the display. Furthermore, the scan converter 116 can be configured to employ analog and/or digital scan converting techniques.

A rendering engine 118, which may include one or more processors, processes the received data. In the illustrated embodiment, the rendering engine 118 includes a view processor 120. As described in greater detail below, the view processor 120, in one instance, combines the data corresponding to different concurrently or serially acquired intersecting planes based on an intersection region of the planes at which the planes intersect. In one instance, the combined data is presented in a perspective, axonometric and/or other three dimensional (3D) view on a two dimensional display screen. Such display may provide a clinician with a 3D view of the two interesting two dimensional slices, or an image that would be present as if the clinician could look at the actual planes in the tissue. As such, the presented view mitigates having the clinician mentally transform multiple two dimensional images to mentally construct a three dimensional image.

In one instance, the view processor 120 of the rendering engine 118 can process real-time data in real-time as the data is acquired and scan converted. In another instance, the view processor 120 of the rendering engine 118 can process previously recorded and stored data. In the illustrated embodiment, the view processor 120 is part of the system 102, for example, implemented via a processor of a console of the system 102. In another embodiment, the view processor 120 is not part of the system 102 and is located remote from the system 102, for example, as a stand alone system or in connection with a computing system. In this embodiment, the acquired data and/or the scan converted data is transferred to the view processor 120 for processing. With such an embodiment, the system 102 can be a conventional US imaging system configured to employ the above-discussed biplane transducer or the like, and the perspective isometric view is generated outside of the system 102.

A user interface 122 includes various input and/or output devices for interacting with the controller 114, for example, to select a data processing and presentation mode (e.g., perspective display), a data acquisition mode (e.g., B-mode), initiate scanning, etc. The user interface 122 may include various controls such as buttons, knobs, a keypad, a touch screen, etc. The user interface 122 may also include various types of visual (e.g., LCD, LED, etc.) and/or audible displays.

Data memory 124 can be used to store data from the receive circuit 112, the scan converter 116 and/or the rendering engine 118, and the rendering engine 118 may obtain data from the data memory to process and render. This includes obtaining, processing and rendering the data during and/or after an imaging procedure is performed. In another embodiment, the data memory 124 is omitted. In yet another embodiment, the data memory 124 is located remote from the system 102.

A display 128 can be used to present the rendered data. In this example, the perspective isometric view is presented via an interactive a graphical user interface (GUI), which allows the user to selectively rotate, scale, and/or move the displayed image within the GUI, and select a transparency level (e.g., from opaque to translucent) for one or more of the planes or subpart of the planes. Such interaction can be through a mouse or the like and/or a keyboard or the like. This includes selecting one or more factory set and/or user customized default displays and/or using free hand tools.

Figure 2:
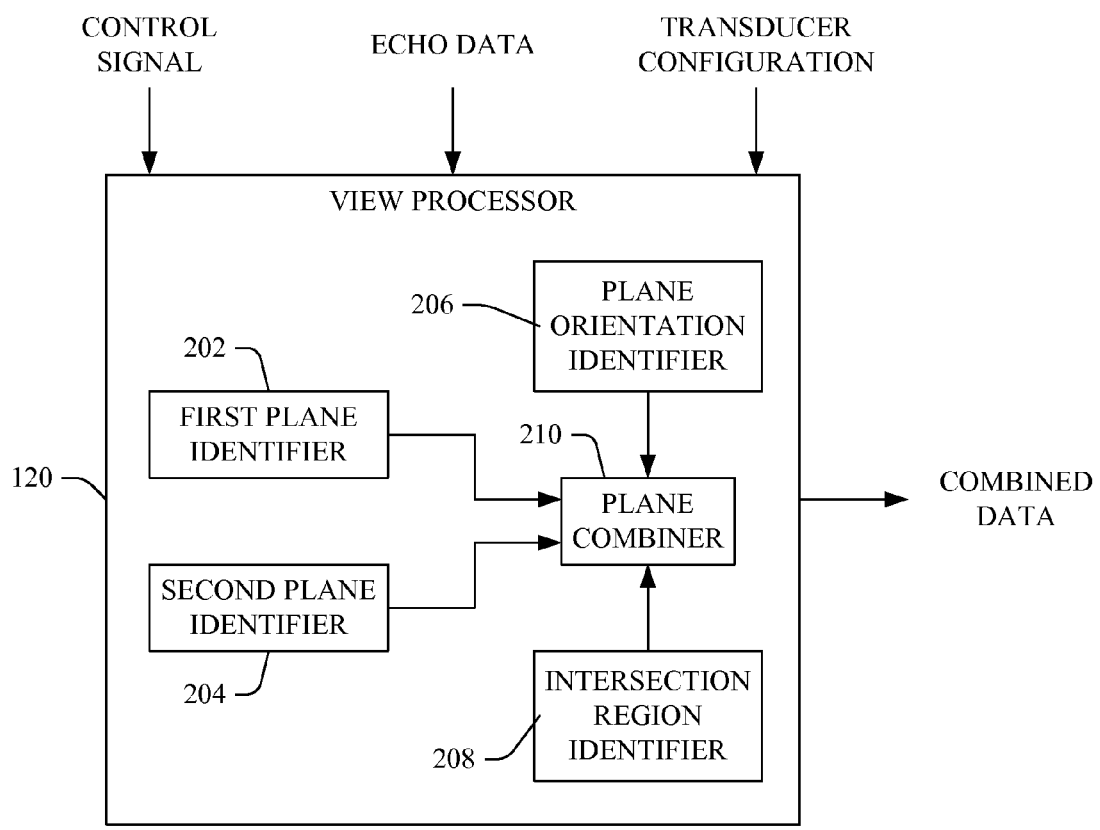
FIG. 2 illustrates an example view processor.

FIG. 2 illustrates an example of the view processor 120 for combining two intersecting image planes. For sake of brevity and explanatory purposes, the intersecting planes are presented in connection with a perspective view. However, as discussed herein, the view processor 120 may additionally or alternatively generate axonometric and/or other three dimensional (3D) views based on the intersecting image planes. In other embodiments, the view processor 120 can be configured to combine more than two planes.

The illustrated view processor 120 includes a first plane identifier 202 and a second plane identifier 204. The first plane identifier 202 identifies and obtains data corresponding to a first plane of the two intersecting planes, and the second plane identifier 204 identifies and obtains data corresponding to a second plane of the two planes. The planes can be obtained from the data from the scan converter 116 and/or the data memory 124 of the system 102 (see FIG. 1).

A plane orientation identifier 206 identifies a spatial orientation or angle between the two intersecting planes and generates a signal indicative thereof. Such information can be obtained from the transducer configuration memory 109, the data itself (e.g., a header, metadata, etc.), and/or user input.

An intersection region identifier 208 identifies an intersection region of the first and second planes at which the first and second regions intersect and generates a signal indicative thereof. Likewise, such information can be obtained from the transducer configuration memory 109, the data itself (e.g., a header, metadata, etc.), and/or user input.

Figure 3:
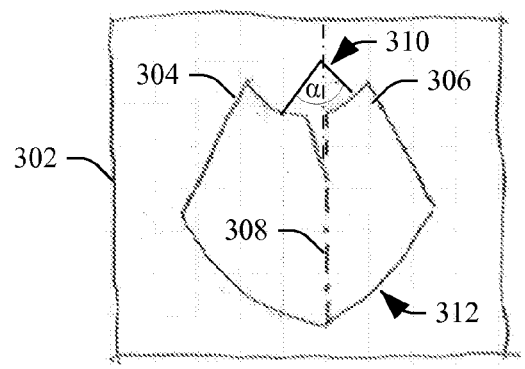
FIG. 3 illustrates an example three dimensional view.

A plane combiner 210 combines the first and second planes based on the signals indicative of the angle between the planes and the plane intersection region to form a single image. In this example, the planes are combined so that the planes are oriented with respect to each other at the angle and so that the planes cross at the intersection region, producing a three dimensional view. FIG. 3 shows an example of an image 302 in which a first plane 304 and a second plane 306 are combined along an intersection region 308 and spatially oriented with respect to each other by an angle (a) 310 therebetween, producing a three dimensional view 312.

Returning to FIG. 2, the resulting image may be well-suited for application in which a three dimensional vision of organs and/or structure is of particular interest. Examples of such applications include, but are not limited to, anesthesia applications in which one image would be used for guiding a needle while another image could be used for maintaining a target position, urological applications in which a three dimensional vision of a lesion cab be acquired for evaluation, etc.

Since the acquired data includes a relatively small volume of data (e.g., two 2D scan planes via 128 elements) which can be acquired at a relatively higher frame rate (e.g., 10 Hz to 50 Hz and greater) the three dimensional perspective image data can be rendered and visualized in connection with color flow, Doppler flow, elastography, contrast harmonic, and/or other information requiring higher data rates. The three dimensional view can also be used in special diagnostic modes (e.g., Histogram, etc.) in which the three dimensional representation may improve the knowledge about a certain identified structure of interest.

For comparative purposes, FIGS. 4A and 4B respectively show the first and second planes 304 and 306 and the intersection region 308 in separated side-by-side images 402 and 404.

Figure 4:
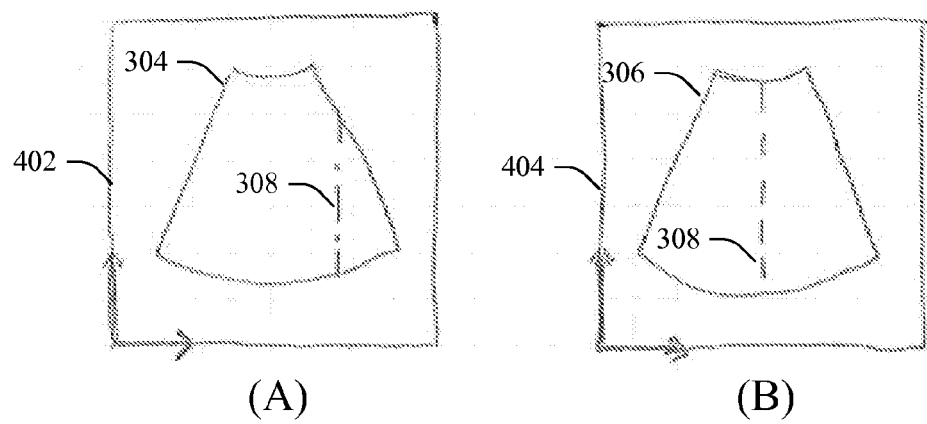
FIG. 4 illustrates side-by-side two dimensional images.
Figure 5:
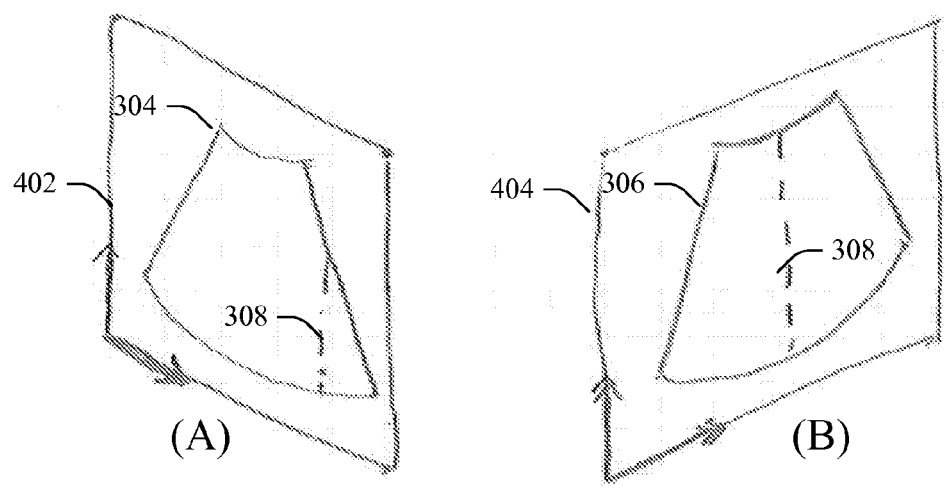
FIG. 5 illustrates side-by-side images two dimensional images, oriented with respect to each other based on relative angle of acquisition therebetween.

Similar to FIG. 4, FIGS. 5A and 5B respectively show the first and second planes 304 and 306 and the intersection region 308 in separated images 402 and 404. However, the images 402 and 404 in FIG. 5 are oriented with respect to each other based on the angle a.

The view processor 120 can additionally or alternatively render images as shown in FIGS. 4 and 5.

Figure 6:
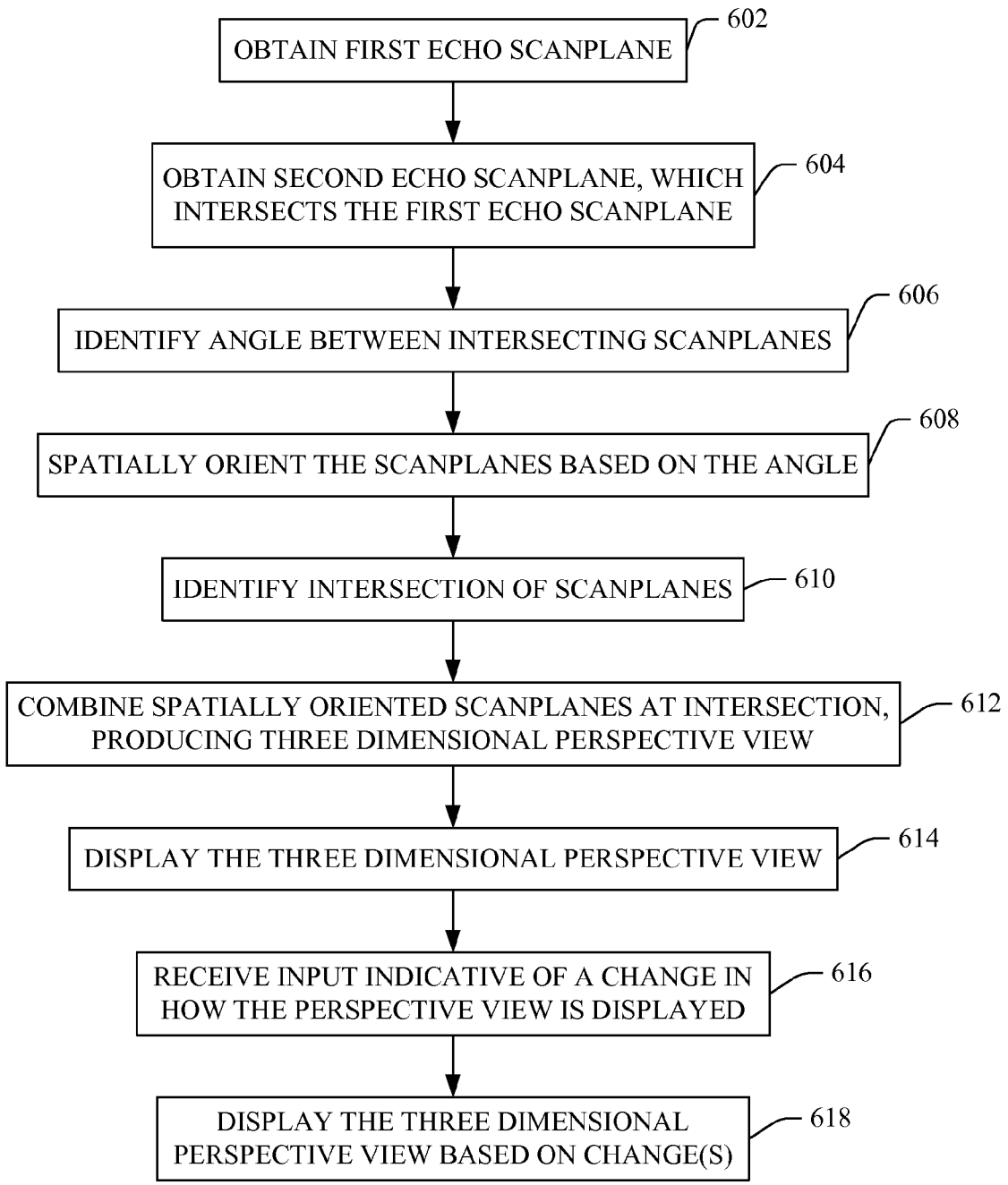
FIG. 6 illustrates an example method.

FIG. 6 illustrates a method for generating a single three dimensional perspective image based on two or more intersecting two dimensional images.

It is to be appreciated that the order of the following acts is provided for explanatory purposes and is not limiting. As such, one or more of the following acts may occur in a different order. Furthermore, one or more of the following acts may be omitted and/or one or more additional acts may be added.

At 602, ultrasound echoes corresponding to a first scanplane are obtained. At 604, ultrasound echoes corresponding to a second scanplane, which intersects the first scanplane, are obtained.

As described herein, the first and second scanplanes may be acquired in an interleaved manner in which scanlines for each of the planes are alternately acquired via a biplane transducer. Furthermore, the scanplanes can be acquired using fast imaging, including at least one of synthetic aperture, plane-wave imaging, or advanced image reconstruction techniques.

At 606, an angle between the first and second scanplanes is identified. As described herein, such information may be provided by the manufacturer and stored in memory accessible to the US scanner.

At 608, the first and second scanplanes are spatially oriented with respect to each other based on the identified angle.

At 610, an intersection region of the first and second scanplanes is identified. As described herein, such information may be provided by the manufacturer and stored in memory accessible to the US scanner.

At 612, the spatially oriented first and second scanplanes are combined at the intersection region to form a single three dimensional perspective image.

At 614, the single three dimensional perspective image is displayed on a monitor or the like.

At 616, optionally, an input indicative of one or more of a rotation, a scaling, a translation, or a transparency for the displayed image is received.

At 618, the single three dimensional perspective image is re-rendered based on the input.

It is to be appreciated that the methods herein may be implemented by one or more processors executing computer executable instructions stored, encoded, embodied, etc. on computer readable storage medium such as computer memory, non-transitory storage, etc. In another instance, the computer executable instructions are additionally or alternatively stored in transitory or signal medium.

Although the above is described in the context of an imaging apparatus such as an ultrasounds imaging apparatus, it is to be understood that other modality imaging apparatuses and non imaging apparatuses that contain an inherent problem of aligning data acquired at different angles or at different phases are also contemplated herein.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A method, comprising:
generating a single three-dimensional perspective or axonometric image based on at least two two-dimensional intersecting scanplanes acquired by two, one-dimensional arrays of a V-shaped biplane transducer, wherein the two, one-dimensional arrays are physically arranged with respect to each other on the transducer in a V-shape in which a distance between the two, one-dimensional arrays tapers along a length of the two, one-dimensional arrays, and the two, one-dimensional arrays are configured for scanning the two two-dimensional intersecting scanplanes.

2. The method of claim 1, wherein the two-dimensional intersecting scanplanes are ultrasound echo images, providing at least one of B-mode, Color Flow, Elastographic, Contrast Harmonic or histologic information.

3. The method of claim 2, where the scanplanes are acquired using synthetic aperture, plane-wave imaging or advanced image reconstruction techniques.

4. The method of claim 1, wherein the two-dimensional intersecting scanplanes are concurrently acquired by different one-dimensional arrays of the biplane ultrasound transducer.

5. The method of claim 4, wherein the two-dimensional intersecting scanplanes are acquired in an interleaved manner in which scanlines for the scanplanes are alternately acquired.

6. The method of claim 1, further comprising:
determining an angle between the at least two two-dimensional intersecting scanplanes; and
generating the single three dimensional perspective image by combining the at least two two-dimensional intersecting scanplanes so that the at least two two-dimensional intersecting scanplanes are oriented with respect to each other at the determined angle.

7. The method of claim 6, further comprising:
determining an intersection region in the at least two two-dimensional intersecting scanplanes at which the a least two two-dimensional intersecting scanplanes intersect; and
generating the single three dimensional perspective image by combining the at least two two-dimensional intersecting scanplanes so that the at least two two-dimensional intersecting scanplanes are spatially oriented with respect to each other at the determined angle and orienting the at least two two-dimensional intersecting scanplanes so that the at least two two-dimensional intersecting scanplanes cross at the intersection region.

8. The method of claim 7, wherein the at least two two-dimensional intersecting scanplanes do not intersects along both of their centerlines.

9. The method of claim 7, wherein the angle is less than ninety degrees.

10. The method of claim 1, further comprising:
generating the single three dimensional perspective image in real time as data used to generate the scanplanes is acquired.

11. The method of claim 1, further comprising:
storing the scanplanes; and
generating the single three dimensional perspective image at a later point in time based on the stored scanplanes.

12. The method of claim 1, further comprising:
employing the three-dimensional perspective image to track a location of moving structure in a scanned object.

13. A rendering engine, comprising:
a view processor that generates a single three dimensional perspective image based on at least two two-dimensional intersecting scanplanes acquired by two, one-dimensional arrays of a V-shaped biplane transducer, the two, one-dimensional arrays comprising:
a first one-dimensional transducer array having a first plurality of elements, a first long axis, first and second ends, and a first transducing surface; and
a second one-dimensional transducer array having a second plurality of elements, a second long axis, first and second ends, and a second transducing surface,
wherein the first and second one-dimensional transducer arrays are disposed in a same plane with the first and second transducing surfaces facing a same direction and with a first distance between respective first ends and a second distance between respective second ends, wherein the first and second distances are different distances and each of the one-dimensional transducers is arranged for scanning the at least two two-dimensional intersecting scanplanes.

14. The engine of claim 13, wherein the two-dimensional intersecting scanplanes are ultrasound echo images.

15. The engine of claim 13, comprising:
a plane orientation identifier, implemented via the view processor, that identifies an angle between the at least two two-dimensional intersecting scanplanes;
an intersection region identifier, implemented via the view processor, that identifies an intersection region at which the at least two two-dimensional intersecting scanplanes intersect; and
a plane combiner, implemented via the view processor, that combines that at least two two-dimensional intersecting scanplanes at the identified intersection region based on the angle.

16. The engine of claim 15, wherein the angle is from a group of angles consisting of an angle from zero to one hundred eighty degrees.

17. The engine of claim 13, wherein one of the scanplanes represents an axial slice through an object or subject being scanned and a second one of the scanplanes represents a slice through a different orientation of the object or subject.

18. The engine of claim 13, wherein the three dimensional perspective image is displayed in connection with one or more of color flow, elastography, contrast harmonic, or histologic information.

19. The engine of claim 13, wherein the view processor generates the three dimensional perspective image in real time as data used to generate the scanplanes is acquired or based on previously stored scanplanes.

20. An ultrasound imaging system, comprising:
a V-shaped biplane transducer array, including two independent one-dimensional transducer arrays, comprising:
a first one-dimensional transducer array having a first plurality of elements, a first long axis, and a first transducing surface; and
a second one-dimensional transducer array having a Second plurality of elements, a second long axis, and a second transducing surface,
wherein the first and second one-dimensional transducer arrays are disposed in a same plane of the V-shaped biplane transducer array with the first and second transducing surfaces facing a same direction and the first and second long axes spatially oriented at a predetermined angle from greater than zero to ninety degrees with respect to each other. and each of the one-dimensional transducers receiving echoes corresponding to different intersecting scanplanes;

a scan converter that scan converts the echoes into a format for display on a monitor; and a view processor that combines the scan converted intersecting scanplanes to form a single three-dimensional perspective or axonometric.

21. The ultrasound imaging system of claim 20, wherein the at least two one-dimensional transducer arrays do not intersect.

22. The ultrasound imaging system of claim 20, wherein the transducer array acquires data at a frame rate between 10 and 200 Hz.

23. The ultrasound imaging system of claim 20, wherein the view processor combines the intersecting scanplanes based on an angle between the scanplanes and an intersection of the scanplanes.

24. The ultrasound imaging system of claim 20, wherein the view processor is implemented via a processor of a console of the ultrasound imaging system.

* * * * *